United States Patent [19]
Frank et al.

[11] Patent Number: 5,281,139
[45] Date of Patent: Jan. 25, 1994

[54] DENTAL EQUIPMENT CLEANING DEVICE

[76] Inventors: Glenn R. Frank, 46 Wakeman Rd., Sherman, Conn. 06784; Stephen C. Dambra, 11 Seymour La., Hopewell Junction, N.Y. 12533

[21] Appl. No.: 6,526

[22] Filed: Jan. 21, 1993

[51] Int. Cl.⁵ .................................................. A61C 1/10
[52] U.S. Cl. ...................................... 433/114; 433/132
[58] Field of Search ................ 433/25, 104, 114, 126, 433/132

[56] References Cited

U.S. PATENT DOCUMENTS

| | | | |
|---|---|---|---|
| 3,494,110 | 2/1970 | Reed et al. | 433/114 |
| 4,149,315 | 4/1979 | Page, Jr. et al. | 433/114 |
| 4,213,243 | 7/1980 | Flatland | 433/126 |
| 4,264,303 | 4/1987 | Rosander | 433/114 |
| 4,398,885 | 8/1983 | Loge et al. | 433/126 |
| 4,877,399 | 10/1989 | Frank et al. | 433/25 |

Primary Examiner—John J. Wilson
Attorney, Agent, or Firm—Patrick J. Walsh

[57] ABSTRACT

An apparatus for driving the turbine and for purging debris from the air and water spray channels of an air driven turbine-type dental handpiece in preparation for sterilizing the handpiece includes a purging chamber for confining the aerosol together with any microorganisms, bacteria, or other contaminents issuing from a handpiece being purged.

4 Claims, 2 Drawing Sheets

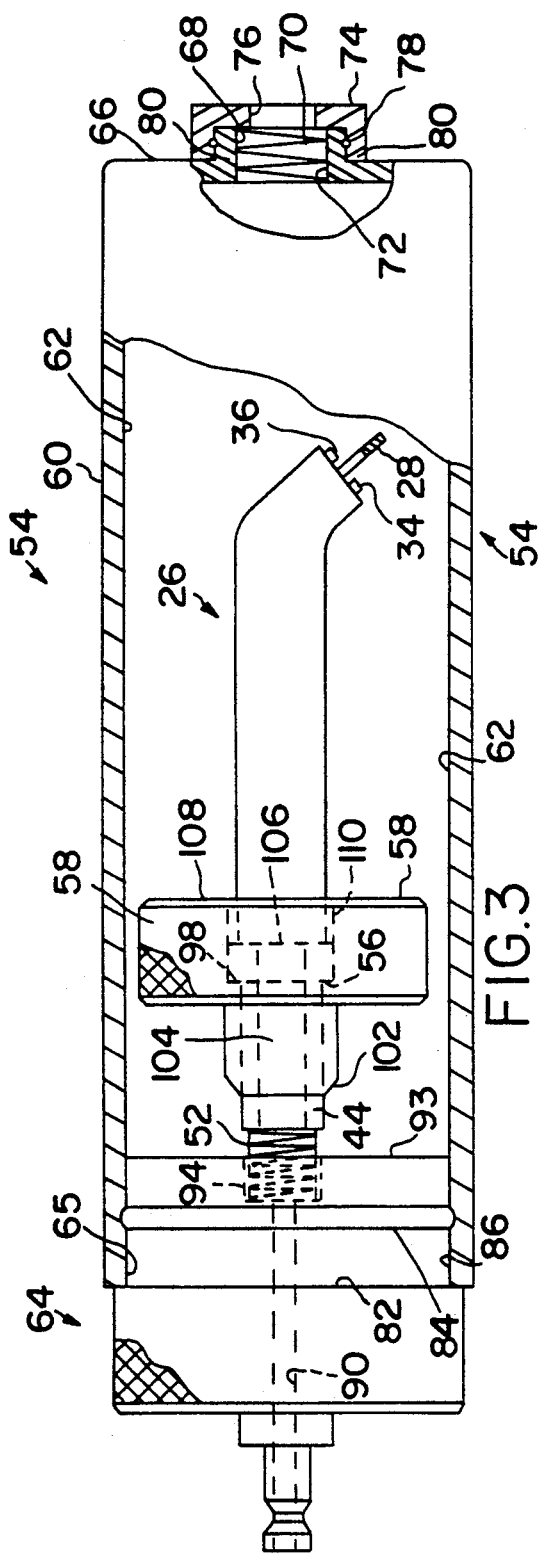
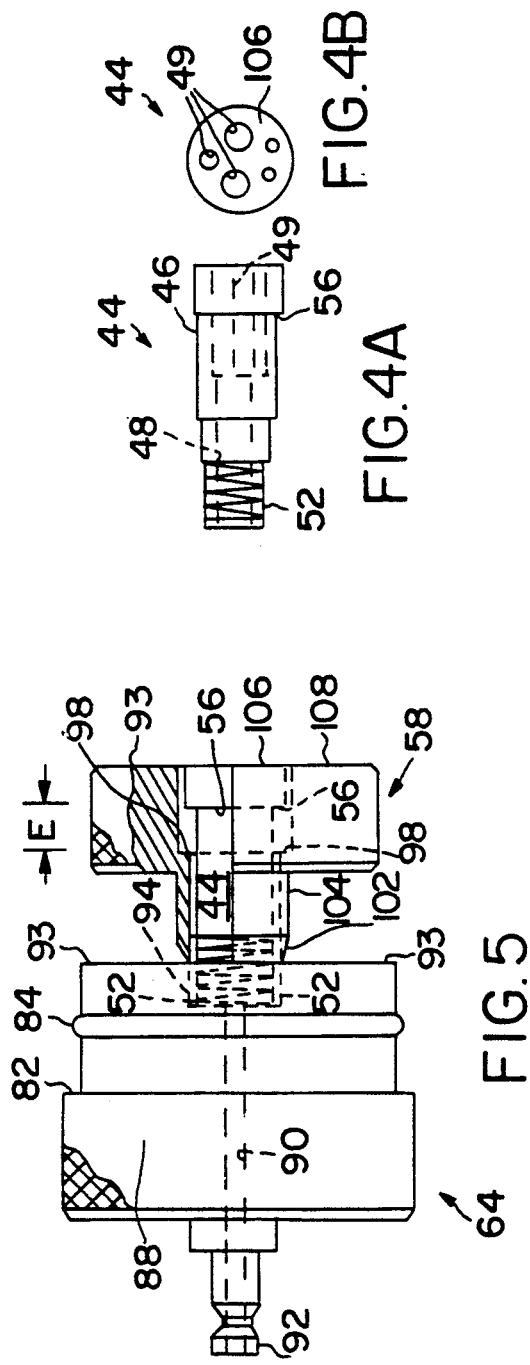

DENTAL EQUIPMENT CLEANING DEVICE

BACKGROUND OF THE INVENTION

The present invention relates to cleaning dental equipment of the type described in U.S. Pat. No. 4,877,399 and in copending application Ser. No. 951,589 filed Sep. 25, 1992.

Dental drills for preparing a cavity for filling comprise a handpiece fitted with an air-driven high speed turbine for rotating a drill or bur. The handpiece also includes internal passages for delivery of high pressure air to the drive turbine, air and water sprays to the mouth, and for a fiber optic system for illuminating the cavity site. In use, the internal passages are susceptible to being blocked with filling or tooth fragments so that the handpiece must be taken out of service and cleaned from time to time.

U.S. Pat. No. 4 877 399 provides a method and apparatus for cleaning the air and water passages including a source of high pressure purging air together with a handpiece adaptor including an insert fitted into the dental handpiece for admitting purging air to the cleaning air and water passages and for blocking passage of purging air to the drive turbine. In this way, the handpiece is quickly prepared for return to service after the purging technique is performed by a member of the dental office staff. As noted in the '399 patent, the insert blocks high pressure purging air to the drive turbine to avoid damaging the turbine.

In addition to purging, manufacturers of dental handpieces fitted with air drive turbines now recommend that after each use a handpiece be cleaned, its turbine lubricated and operated with drive air, and sterilized. Copending application Ser. No. 951,589 provides a handpiece adaptor enabling a dental office to lubricate and operate handpiece turbines in the sterilization area of the office as well as to purge air and water lines of the handpiece. In this way thorough cleaning and sterilization of handpieces following manufacturers recommendations may be accomplished through uninterrupted flow of sterilization/asepsis procedures already existing in a typical dental office.

In using the handpiece adaptor, the handpiece is removed from the dental console after use and brought to the sterilization area of the dental office. The handpiece is cleaned externally and its turbine lubricated. The adaptor is fitted to the handpiece establishing through passages with the air and water spray passages, and with turbine air drive and exhaust passages. High pressure air is applied to the handpiece through the adaptor for purging the air and water spray channels, and for driving the turbine. Turbine drive air flows through the supply passage, drives the turbine, and returns through the adaptor exiting to ambience through an exhaust port in the adaptor. Next, the handpiece is sterilized in an autoclave, for example, and returned to service.

In using the handpiece adaptor the flow of high pressure air through the handpiece creates an aerosol which gives rise to the possibility of spreading a cloud of airborne microorganisms or bacteria released from the air and water passages of the handpiece. There is a potential hazard for dental office personnel particularly in the sterilization area of the office of exposure to contagious disease such as tuberculosis, AIDS, and so forth picked up by a dental handpiece from a dental patient. The invention provides a device for eliminating aerosol propagation of bacteria or microorganisms or other contaminants released from dental handpieces.

SUMMARY OF THE INVENTION

The present invention provides for safe cleaning of dental handpieces involving the pressurized air purging of the air and water passages as well as operation of the handpiece turbine in the course of cleaning and sterilizing the handpiece in a dental office.

In accordance with the invention, the handpiece is enclosed within a purging chamber and connected to pressurized air through the handpiece adaptor of application Ser. No. 951,589. Pressurized air is then applied to the water and air passages and the drill turbine for cleaning the handpiece. The resultant aerosol and any entrained bacteria or microorganism are confined to the interior of the purging chamber. The chamber includes a filtered port to ambience for venting the chamber and maintaining atmospheric pressure therein.

In a preferred form of the invention, the handpiece adaptor is incorporated into the purging chamber to facilitate the cleaning of handpieces and the subsequent sterilization of handpieces and the purging chamber. The purging chamber includes a removable closure cap with a central air passage containing the handpiece adaptor and a coupling for quickly connecting and disconnecting the handpiece for purging in the chamber.

After purging, the dental handpieces are sterilized and the purging chamber is included along with the handpieces in the batch of instruments being sterilized.

As a result, the potential for propagation of airborne microorganisms and bacteria while cleaning handpieces is eliminated.

OBJECTS OF THE INVENTION

It is an object of the invention to provide means for enabling safe cleaning and sterilization of dental handpieces in a dental office.

It is an object of the invention to provide an aerosol chamber for dental handpieces so that the handpiece can be safely cleaned and sterilized utilizing pressurized air.

It is a further object of the invention to provide a purging chamber for dental handpieces incorporating a handpiece adaptor through which air and water spray passages can be purged and the drive turbine operated without releasing an aerosol having the potential for propagating bacteria or microorganisms in the sterilization area of a dental office.

It is a further object of the invention to provide a dental handpiece purging chamber which can be sterilized along with handpieces.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which:

FIG. 3 is a side elevation view partly in section of a purging chamber according to the invention.

FIGS. 4a and 4b are respectively side elevation and end views of a handpiece adaptor used with the invention.

FIG. 5 is a side elevation view partly in section of the closure cap incorporating the handpiece adaptor for use with the purging chamber of the invention.

DETAILED DESCRIPTION OF THE INVENTION

Figure 1:
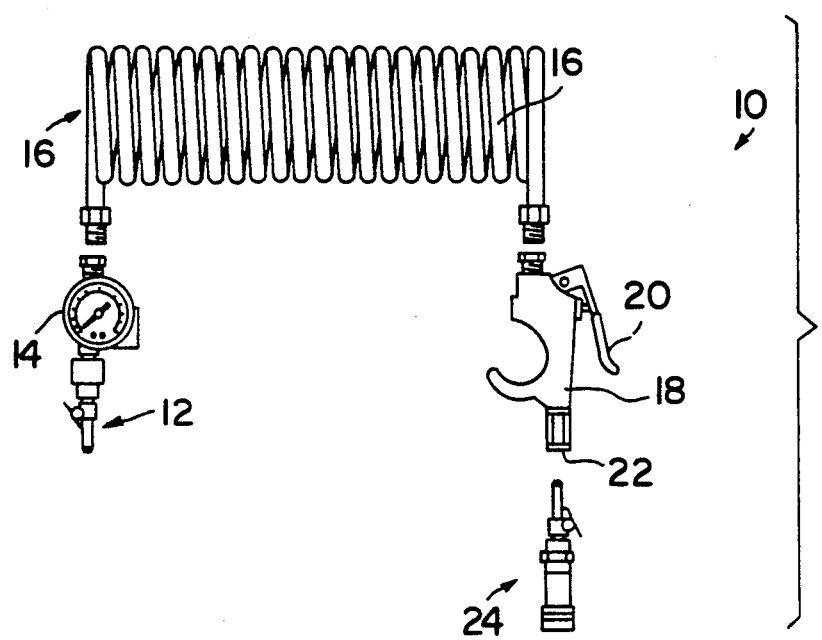
FIG. 1 illustrates a set of dental equipment cleaning components used with the present invention.

Referring now to the drawing, the invention forms part of a dental equipment cleaning kit shown in FIG. 1 and comprises a compressed air system 10 for connection to compressed air service available in the dental office. The kit defining the compressed air system includes an inlet connector 12 to the air service, a pressure regulator and gauge 14, an air hose 16, a manually operated air valve 18 with actuating lever 20, and a quick connect fitting 22 for receiving a purging chamber 24 according to the invention.

Figure 2:
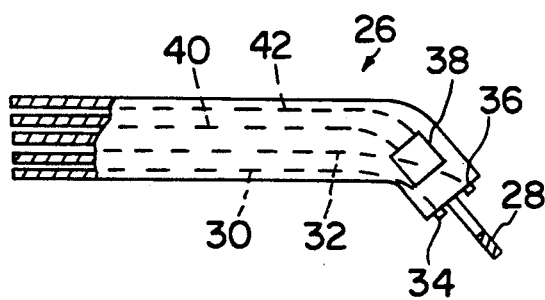
FIG. 2 is a side view partly in section of a dental handpiece fitted to a handpiece adaptor.

A dental handpiece 26, as shown in FIG. 2, includes a drilling bur 28 and internal passages 30, 32 for supplying spray air and water through openings 34, 36 located in the vicinity of the bur. The hand piece further includes a drive turbine 38 for rotating the bur powered by compressed air supplied through an internal passage 40. An exhaust passage 42 receives and returns exhaust drive air through the handpiece. In accordance with manufacturers recommendation, the drive turbine must be lubricated and operated using compressed air prior to sterilization. The handpiece is connected to an adaptor as described in copending application Ser. No. 951,589. In a preferred embodiment of the adaptor suitable for use with the present invention and shown in FIGS. 4a and 4b, the adaptor 44 includes a tubular body 46 with an inlet air passage 48 and purging air passages 49 for the handpiece 26. The adaptor outer body surface includes a threaded tip 52 for connection to a purging chamber 54 and an annular shoulder 56 for retaining a captive handpiece coupling 58 as described below.

In accordance with the invention, the handpiece is enclosed within a purging chamber while being cleaned. The purging chamber 54 includes a cylindrical body 60 with an interior purging chamber 62 and a closure cap 64 for enclosing an open end 65 of the chamber and mounting a handpiece within the chamber. The cylindrical body end wall 66 includes a filter opening 68 for receiving a porous filter 70 within the bore 72 of the opening. A filter cap 74 with a vent opening 76 retains the filter in place in the chamber end wall. The filter cap shown is provided with an O-ring 78 for a secure fit as the cap is installed over a retaining collar 80 about the filter.

The purging chamber assembly of FIG. 3 illustrates the closure cap 64 in normal position with a handpiece 26 in place ready for purging with pressurized air. The closure cap 64 includes a shoulder 82 and O-ring 84 for air tight fit with the interior surface 86 of the purging chamber.

The closure cap shown also in FIG. 5 is a cylindrical block 88 with a central longitudinal bore 90 defining a purging air passage with an entrance quick connect fitting 92 for connection to counterpart fitting 24 of the air supply kit of FIG. 1. The inner face 93 of the closure cap includes a threaded bore 94 receiving the threaded tip 52 of the handpiece adaptor 44 in communication with the inlet air passage 90.

A captive coupling 58 fits over the adaptor 44 for mounting dental handpiece 26 to the adaptor with internal passages aligned. The adaptor and coupling are a subassembly secured to the closure cap as a unit by the threaded tip 52 of the adaptor and the threaded bore 94. The coupling rotates freely on the adaptor. The coupling is also slidably mounted on the adaptor for limited axial movement defined at one end by abutment of adaptor outer shoulder 56 with coupling interior shoulder 98, and at the other end by the tip 102 coupling sleeve 104 abutting the closure cap inner face 93. The excursion E of the captive coupling is evident from a comparison of FIGS. 3 and 5. In FIG. 5, the coupling is slidably retracted and the outer face 106 of the adaptor is exposed at the end face 108 of the coupling for receiving a handpiece. In FIG. 3, the coupling is advanced into position onto the threaded tip 110 of the handpiece firmly holding the handpiece within the purging chamber. In this way, the coupling engages and secures the handpiece to the adaptor by a firm threaded connection. The limited axial and free rotary movement of the coupling facilitate quick and easy securing of the handpiece to the adaptor.

In operation, the handpiece is removed from the dental console after each use for sterilization as required by public health standards in many jurisdictions. The handpiece is cleaned externally and its turbine lubricated. The handpiece is fitted to the handpiece adaptor for establishing passages through the adaptor insert with the air and water spray passages, and with turbine air drive and exhaust passages. The coupling is secured to the handpiece holding it securely in place. Next, the purging chamber is fitted onto the closure cap in covering relation to the handpiece. Regulated air pressure air of 30-40 psi from office air service is taken by the cleaning kit and applied to the handpiece through the adaptor for purging the air and water spray channels, and for driving the turbine. An aerosol is created issuing from the openings in the vicinity of the bur and from the turbine drive exhaust port in the adaptor. The aerosol entrained with any bacteria or microorganisms and any other airborne contaminants as may have been lodged in the handpiece is entirely confined to the purging chamber. Overpressure within the chamber is dissipated through the filter without releasing any contaminant to ambience of the sterilization area of the office. Next, the handpiece is sterilized along with the purging chamber and its components in an autoclave, for example, and returned to service. The purging chamber may be used to purge several handpieces before it is sterilized. For example, the chamber can be sterilized with a batch of handpieces or used for purging through the day and the sterilized before closing.

It will be understood that the cleaning kit together with the handpiece adaptor and purging chamber enable staff to perform the required preparation of the handpiece for sterilization including turbine lubrication and operation at the sterilization station within the office and without hazard arising from aerosol spread of contaminants in the sterilization area. In this way, handpieces may be routinely cleaned and sterilized in compliance with newly established standards without any revisions to dental office installations or routine.

We claim:

1. An apparatus for purging debris from a dental handpiece with compressed air, the handpiece having turbine drive-air supply and exhaust channels, a cleaning water channel, and a cleaning air channel comprising an air line including a source of compressed air, means for regulating the source of compressed air to a safe level, a valve member, an air hose interconnecting the regulating means and the valve member, and means for opening and closing the valve member, a purging chamber including a body member defining an interior chamber, means for venting the interior chamber to ambience, a closure cap for closing the interior chamber, means for mounting the handpiece within the chamber, a handpiece adaptor for interconnecting the air line to a dental handpiece, so that when the handpiece is purged with compressed air, the aerosol issued from the handpiece is confined to the interior chamber.

2. An apparatus for purging debris from a dental handpiece with compressed air, the handpiece having turbine drive-air supply and exhaust channels, a cleaning water channel, and a cleaning air channel comprising an air line including a source of compressed air, means for regulating the source of compressed air to a safe level, a valve member, an air hose interconnecting the regulating means and the valve member, and means for opening and closing the valve member, a purging chamber including a body member defining an interior chamber, a closure cap for closing the interior chamber, the closure cap having an air passage for connection to the source of compressed air for introducing compressed air to the interior chamber, a handpiece adaptor secured to the closure cap for interconnecting the air passage to a dental handpiece, and a coupling mounted on the adaptor for securing the handpiece to the adaptor within the chamber so that when the handpiece is purged with compressed air the aerosol issued from the handpiece is confined to the interior chamber.

3. An apparatus as defined in claim 2 in which the purging chamber includes a filtered vent to ambience.

4. An apparatus for purging a dental handpiece with compressed air comprising an air line including a source of compressed air, means for regulating the source of compressed air to a safe level, a valve member, an air hose interconnecting the regulating means and the valve member, and means for opening and closing the valve member, a purging chamber including a body member defining an interior chamber open at one end and having a filtered vent opening through the body member to ambience, a closure cap for closing the open end of the interior chamber, the closure having a longitudinal air passage and an inlet fitting for admitting compressed air to the interior chamber, a handpiece adaptor secured to the closure cap for interconnecting the air passage to a dental handpiece, a captive coupling mounted on the adaptor in free rotary and limited axial movement for securing a handpiece to the adaptor within the chamber so that when the handpiece is purged with compressed air the aerosol issued from the handpiece is confined to the interior chamber.

* * * * *